United States Patent
Deng et al.

(10) Patent No.: US 11,002,736 B2
(45) Date of Patent: May 11, 2021

(54) USE OF SUSD2 PROTEIN AS MARKER

(71) Applicants: PEKING UNIVERSITY, Beijing (CN); PEKING UNIVERSITY SHENZHEN GRADUATE SCHOOL, Guangdong (CN); BEIJING RUIPU CHENCHUANG TECHNOLOGY CO., LTD., Beijing (CN)

(72) Inventors: Hongkui Deng, Beijing (CN); Haisong Liu, Beijing (CN); Dicong Zhu, Beijing (CN); Huan Yang, Beijing (CN); Zhen Liang, Beijing (CN)

(73) Assignees: PEKING UNIVERSITY, Beijing (CN); PEKING UNIVERSITY SHENZHEN GRADUATE SCHOOL, Guangdong (CN); BEIJING RUIPU CHENCHUANG TECHNOLOGY CO., LTD., Beijing (CN)

( * ) Notice: Subject to any disclaimer, the term of this patent is extended or adjusted under 35 U.S.C. 154(b) by 89 days.

(21) Appl. No.: 15/501,616

(22) PCT Filed: Aug. 4, 2015

(86) PCT No.: PCT/CN2015/085990
§ 371 (c)(1),
(2) Date: Feb. 3, 2017

(87) PCT Pub. No.: WO2016/019842
PCT Pub. Date: Feb. 11, 2016

(65) Prior Publication Data
US 2017/0227539 A1    Aug. 10, 2017

(30) Foreign Application Priority Data

Aug. 7, 2014 (CN) .......................... 201410386506.0

(51) Int. Cl.
| | |
|---|---|
| *G01N 33/53* | (2006.01) |
| *C12Q 1/6883* | (2018.01) |
| *C12Q 1/6886* | (2018.01) |
| *G01N 33/569* | (2006.01) |
| *G01N 33/50* | (2006.01) |
| *G01N 33/543* | (2006.01) |
| *G01N 33/58* | (2006.01) |

(52) U.S. Cl.
CPC ..... *G01N 33/56966* (2013.01); *G01N 33/507* (2013.01); *G01N 33/5073* (2013.01); *G01N 33/54326* (2013.01); *G01N 33/582* (2013.01); *G01N 2333/705* (2013.01); *G01N 2500/10* (2013.01)

(58) Field of Classification Search
None
See application file for complete search history.

(56) References Cited

U.S. PATENT DOCUMENTS

| | | | |
|---|---|---|---|
| 7,842,467 B1* | 11/2010 | Heidbrink | G01N 33/57415 435/7.1 |
| 9,526,749 B2 | 12/2016 | Walker et al. | |
| 2007/0099251 A1* | 5/2007 | Zhang | G01N 33/574 435/7.23 |
| 2009/0269774 A1* | 10/2009 | Rothenberg | G01N 33/6893 435/6.11 |
| 2015/0010516 A1 | 1/2015 | Buehring et al. | |

FOREIGN PATENT DOCUMENTS

| | | |
|---|---|---|
| CN | 102321572 A | 1/2012 |
| CN | 104215768 A | 12/2014 |
| WO | WO 2012/070014 | 5/2012 |
| WO | 2013139952 A2 | 9/2013 |
| WO | 2014030166 A1 | 2/2014 |

OTHER PUBLICATIONS

Sivasubramaniyan et al. ("Prospective Isolation of Mesenchymal Stem Cells from Human Bone Marrow Using Novel Antibodies Directed Against Sushi Domain Containing 2", Stem Cells and Development, vol. 22, No. 13, pp. 1944-1954, published Feb. 13, 2013) (Year: 2013).*
Karaoz et al. ("Isolation and characterization of stem cells from pancreatic islet: pluripotency, differentiation potential and ultra-structural characteristics," (Cytotherapy, vol. 12, pp. 288-302, published 2010). (Year: 2010).*
NCBI Reference Sequence: NP_062547.1 sushi domain-containing protein 2 precursor [*Homo samiens*], (2016), https://www.ncbi.nlm.nih.gov/protein/NP_062547.1.
Liu, et al. "Systematically labeling developmental stage-specific genes for the study of pancreatic b-cell differentiation from human embryonic stem cells", Cell Research 14, (2014), pp. 1181-1200.
Search Report issued in European Patent Application No. 15829144.3, dated Nov. 23, 2017.

* cited by examiner

*Primary Examiner* — Tracy Vivlemore
*Assistant Examiner* — Nam P Nguyen
(74) *Attorney, Agent, or Firm* — Norton Rose Fulbright US LLP; James R. Crawford

(57) ABSTRACT

SUSD2 protein is used as a marker in identification, selection or separation of pancreatic internal secretion precursor cells and/or newborn pancreatic internal secretion cells; and a use of an mRNA, for encoding the SUSD2 protein, of a precursor protein as the marker in identification of the pancreatic internal secretion precursor cells and/or the newborn pancreatic internal secretion cells. Analysis of gene expression of pancreatic endoderm cells sourced by induced directional differentiation of human pluripotent stem cells finds the enrichment expression of a SUSD2 gene in the pancreatic internal secretion precursor cells and the newborn pancreatic internal secretion cells. A protein encoded by the SUSD2 gene is a receptor protein on cell membranes. Using the protein as the marker, the identification, the selection or the separation of the pancreatic internal secretion precursor cells and the newborn pancreatic internal secretion cells can be conducted.

1 Claim, 11 Drawing Sheets

Specification includes a Sequence Listing.

(a)

(b)

(a)

(b)

(a)

(b)

(a)

(a)

(b)

USE OF SUSD2 PROTEIN AS MARKER

This application is a Section 371 of PCT Application No. PCT/CN2015/085990 filed Aug. 4, 2015, and claims priority under Section 119 from Chinese Patent Application No. 201410386506.0 filed on Aug. 7, 2014, each of which is incorporated by reference in its entirety.

TECHNICAL FIELD

The present invention relates to the field of biotechnology, and in particular to the use of the SUSD2 protein as a marker.

BACKGROUND ART

Human pluripotent stem cell-derived pancreatic beta-cells provide sufficient sources of donor islet cells for use in cell replacement therapy for diabetes, particularly for type I diabetes. In addition, the directed differentiation of human pluripotent stem cells (hPSCs) into pancreatic beta-cells can also provide a model for studying human pancreatic development in vitro. The process of the directed differentiation of hPSCs into pancreatic beta-cells can be divided into several stages by mimicking development events in vivo: definitive endoderm, gut tube, posterior foregut, pancreatic endoderm, and pancreatic endocrine cells. Among them, pancreatic endoderm cells are mixed cell populations, usually including pancreatic progenitor cells, pancreatic endocrine progenitor cells and nascent pancreatic endocrine cells and the like. The cell fate is determinate by detecting the expression of pancreatic development-related genes. Pancreatic progenitor cells are mainly indicated by expression of the relevant genes such as PDX1, HNF1B, SOX9, NKX6.1, HNF6 and so on. NGN3 is the most important marker gene of pancreatic endocrine progenitor cells, and however, due to its transient expression characteristics, it is required to combine with the expression of its downstream genes such as NKX2.2 and NEUROD1, as well as negative expression of endocrine-related genes such as CHROMOGRANIN A, INSULIN, and GLUCAGON to indicate the fate of pancreatic endocrine progenitor cells. Although the expression of these marker genes can be used to indicate the fate of specific cells, the expression of these proteins cannot be used to isolate and purify specific cell populations as they are all transcription factors or secretory proteins, generally locating within the cytoplasm or nucleus, in particular human pancreatic endocrine progenitor cells and nascent pancreatic endocrine cells, so that their molecular characteristics cannot be studied in more detail.

At present, pancreatic progenitor cells can be obtained by directed differentiation of hPSCs, however, these cells differentiated into functional mature pancreatic beta-cells with low efficiency in vitro. Although after pancreatic precursor cells derived from human pluripotent stem cells are transplanted into immunodeficient mouse, functionally mature islet cells can be obtained, due to the proliferative capacity of pancreatic precursor cells, their tumorigenicity limits their promotion to clinical application. The functional mature beta-cells are more desirable donor cell sources than pancreatic progenitor cells. However, how to differentiate pancreatic progenitor cells into functional mature beta-cells in vitro greatly limits the implementation of alternative treatment of diabetes cells, while in the differentiation process from pancreatic precursor cells to pancreatic beta-cells, the most important step is the correct realization of efficient induced differentiation of pancreatic endocrine precursor cells. Studies on animal model such as mouse have greatly promoted the understanding of the development of pancreatic beta-cells. These studies have played a decisive role in directing the directed differentiation of pancreatic beta-cells in vitro. In spite of this, studies on the fate specialization of pancreatic endocrine precursor cells and the fate selection between different endocrine cells are still few. In addition, there exist some species differences between human and model animal such as mouse. Therefore, finding relevant molecular markers to directly isolate pancreas-related cells at a particular developmental stage for researching can significantly speed up the acquisition of functional mature pancreatic beta-cells in vitro.

SUMMARY

It is an object of the present invention to provide a method for sorting or assisting the sorting of pancreatic endocrine progenitor cells or nascent endocrine cells in a population of cells to be tested.

The method provided by the present invention comprises the following steps: detecting whether the cells in the population of cells to be tested express SUSD2 gene; if some cells express the SUSD2 gene, these cells are or are candidates for pancreatic endocrine precursor cells or nascent endocrine cells; If some cells do not express the SUSD2 gene, these cells are not or are not candidates for pancreatic endocrine precursor cells or nascent endocrine cells.

The nucleotide sequence of the SUSD2 gene is illustrated as SEQ ID NO: 2 in the Sequence Listing.

In the above method, the step of detecting whether the cells in the population of cells to be tested express a SUSD2 gene is performed by detecting whether the cell in the population of cells to be tested contains a protein expressed by the SUSD2 gene, and the method for detecting whether the cell in the population of cells to be tested contains the protein expressed by the SUSD2 gene is as following 1) or 2) or 3):

1) immunofluorescence antibody assay, using anti-SUSD2 monoclonal antibody;
2) flow cytometry, using anti-SUSD2 monoclonal antibody;
3) magnetic beads cell sorting, using anti-SUSD2 monoclonal antibody.

In the above method, the cells to be tested are pancreatic endoderm cells.

In the above method, the pancreatic endoderm cell is human-derived pancreatic endoderm cells.

By analyzing gene expression profiles of the pancreatic endoderm cells, the present inventors also find that the expression of the SUSD2 gene is enriched in pancreatic endocrine progenitor cells and neonatal endocrine cells, i.e., SUSD2 protein can be used as the molecular marker of the both cells.

Based on the above findings, the present invention provides the use of a SUSD2 protein as a marker in the identification, screening or sorting of pancreatic endocrine progenitor cells and/or nascent pancreatic endocrine cells, wherein the amino acid sequence of the SUSD2 protein is shown as SEQ ID NO: 1.

NCBI Reference Sequence of the SUSD2 protein is NP_062547.1.

The nascent pancreatic endocrine cells refer to a population of hormone (including Insulin, Glucagon, Ghrelin, Pancreatic Polypeptide, Somatostatin, etc.)-positive cells during the process of direct differentiation from human pluripotent stem cells into pancreatic beta-cells. This cell population usually co-expresses multi-hormone, and are less mature functionally as compared to mature pancreatic endocrine cells. During in vivo development, nascent pancreatic endocrine cells are primarily pancreatic endocrine cells that are functionally immature during embryonic development.

The present invention also provides use of an antibody capable of specifically binding to a SUSD2 protein in preparation of a reagent for identification, screening or sorting of pancreatic endocrine precursor cells and/or nascent pancreatic endocrine cells.

The SUSD2 protein is a protein expressed by the SUSD2 gene, which is neither a transcription factor nor a secretory protein, but a receptor protein located on cell membrane.

The cells to be tested are detected by immunofluorescent antibody method to determine whether they expressed SUSD2 proteins or not, in order to determine whether the cells to be tested are pancreatic endocrine precursor cells or nascent pancreatic endocrine cells.

The antibody may be selected from an intact antibody molecule, a chimeric antibody, a single chain antibody, a bispecific antibody, a heavy chain of an antibody, a light chain of an antibody, homodimer and heterodimer of heavy and light chains, antigen binding fragment, and their derivatives. The intact antibody molecule can be a polyclonal or monoclonal antibody, preferably a monoclonal antibody.

As described above, the SUSD2 protein can generally be detected by an immunofluorescent antibody method, wherein the antibody against the protein or a secondary antibody against the antibody is required to carry a corresponding fluorescent label.

The pancreatic endocrine precursor cells and nascent pancreatic endocrine cells are a population of cells in pancreatic endoderm cells, which can produce functionally mature pancreatic endocrine cells under suitable conditions.

The human pancreatic endoderm cells mainly refer to the cells at pancreatic endoderm stage during the process of direct differentiation from human pluripotent stem cells to pancreatic beta-cells, or human embryonic pancreatic tissue cells at corresponding developmental stage which are freshly isolated and have been cultured in vitro, mainly comprising pancreatic precursor cells, pancreatic endocrine precursor cells and nascent pancreatic endocrine cells. The primary object of the present invention is to screen or sort pancreatic endocrine precursor cells and nascent pancreatic endocrine cells from pancreatic endoderm cell populations.

The sources of pancreatic endoderm cells include: 1. cells obtained by direct differentiation from human pluripotent stem cells; 2. cells obtained from isolated human embryonic pancreas tissue; 3. cells obtained by in vitro culture of isolated human embryonic pancreatic endoderm cells.

The method for screening or sorting mainly adopts immunomagnetic separation or flow cytometry sorting.

In the process of SUSD2 gene expression, it is first transcribed into mRNA, then the mRNA is translated into SUSD2 precursor protein, and then the precursor protein is processed to produce mature SUSD2 protein.

For the above reasons, the present invention also provides a use of an mRNA encoding a precursor protein of a SUSD2 protein as a marker in identification of pancreatic endocrine precursor cells and/or nascent pancreatic endocrine cells.

The invention further provides the use of a primer, probe or their complementary strands capable of specifically binding to the mRNA in preparation of a reagent for identification of pancreatic endocrine precursor cells and/or nascent pancreatic endocrine cells.

The primer may be a primer for amplifying the whole mRNA or a primer for amplifying a characteristic region of the mRNA, and the probe is a nucleotide which recognizes a specific region of the mRNA and generally carries a label.

According to the description of the examples, the present invention provides a pair of primers that specifically amplify the mRNA, as follows:
upstream primer: GGCACCGCCAACACCTCA
downstream primer: GCGTGGGCAGCGACTTGA.

The method for identification may employ fluorescence quantitative PCR.

By analyzing the gene expression profiles of the endoderm cells, the inventors find that the expression of SUSD2 gene is enriched in the pancreatic endocrine precursor cells and nascent pancreatic endocrine cells, and its encoded protein is a receptor protein on a cell membrane and the protein can be used as a marker to identify, screen or sort pancreatic endocrine precursor cells and nascent pancreatic endocrine cells, which is of great significance for the study of pancreas-related cells at various developmental stages.

DETAILED DESCRIPTION

Figure 1:
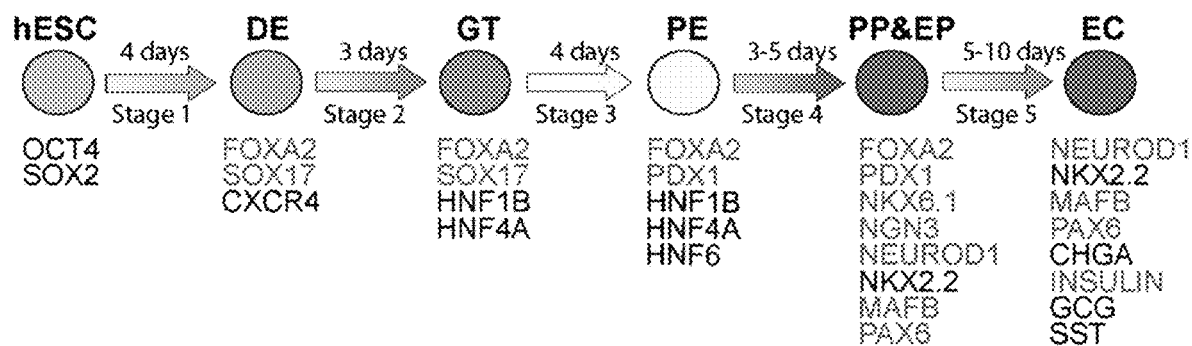
FIG. 1 shows the direct differentiation from human pluripotent stem cells into pancreatic endoderm cells. (a) Schematic representation of direct differentiation from human pluripotent stem cells into pancreatic beta-cells; (b) immunofluorescent staining for detecting the expression of green fluorescent protein (EGFP) marking NGN3 genes and pancreatic endoderm-related proteins at the end of the stage 4 of differentiation.
Figure 1:
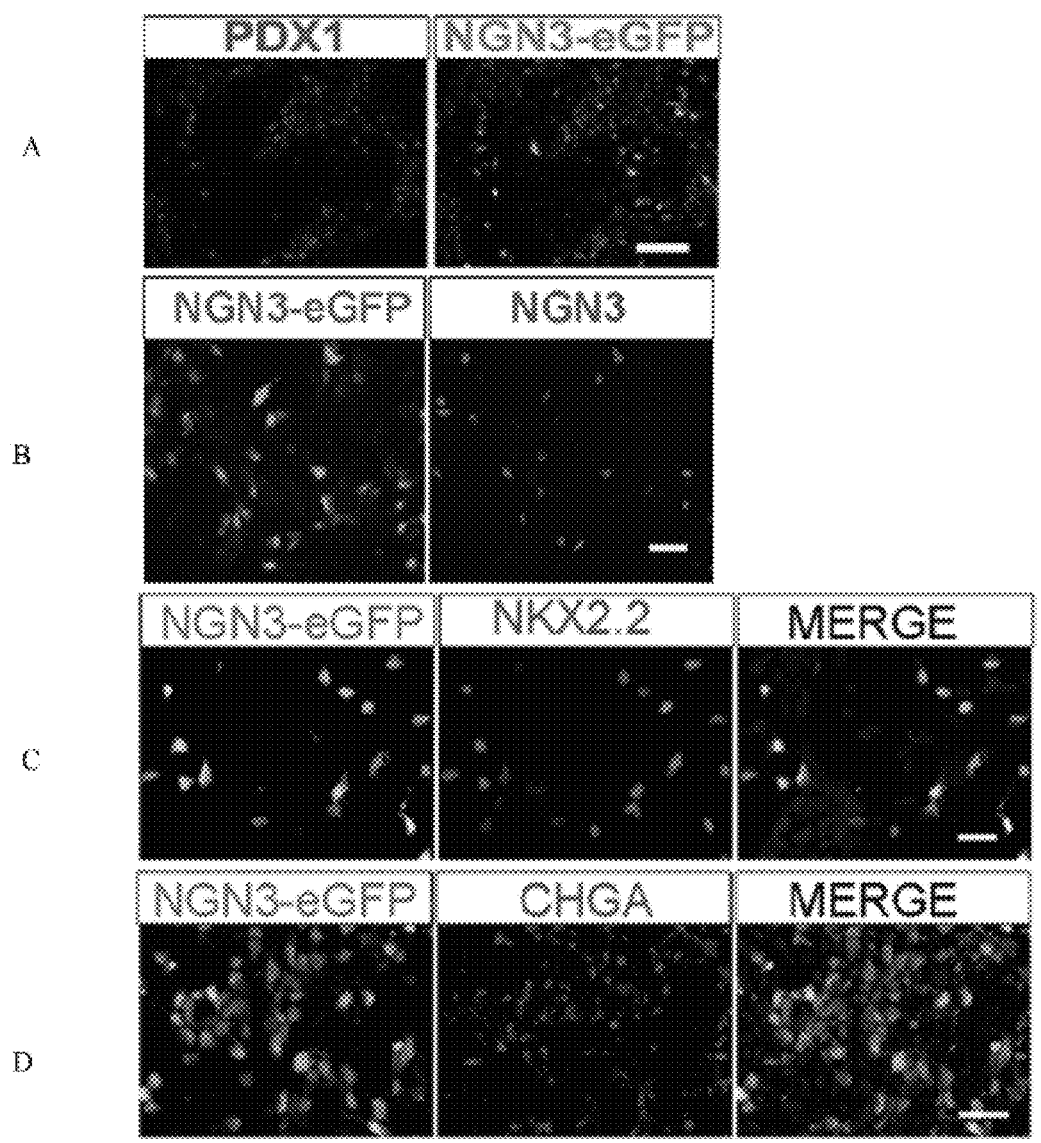

All of the experimental methods used in the following examples are conventional methods unless otherwise specified. All of the materials, reagents and the like used in the following examples are commercially available unless otherwise specified. The SUSD2 gene is shown in SEQ ID NO: 2 and the amino acid sequence of the encoded protein is SEQ ID NO: 1.

Example 1: Discovery and Application of SUSD2 as a Marker Gene for Pancreatic Endocrine Precursor Cells 1. SUSD2 as a Marker Gene of Pancreatic Endocrine Precursor Cells Obtained by Differentiation of Modified Human Pluripotent Stem Cells 1.1 Acquisition of the Pancreatic Endoderm Cell The EGFP gene (NC_013179.1 (3313 . . . 4126)) was homologously recombined (Ngn3contig No.: NT_030059.13, located in the Chromosome 10, the position of the left homologous arm in the genome: 71325654-71332154; the position of the right homologous arm in the genome: 71332158-71467568) into an isolated human pluripotent stem cell line H1 (WiCell Research Institute, NIH No.: WA01) to obtain the modified human pluripotent stem cell line NGN3-EGFP. The cells were seeded into cell culture solution I in 15%-20% and cultured for 1 day; then directly transferred into cell culture solution II and cultured for 1-2 days; subsequently directly transferred into cell culture solution III and cultured for 1 day; then directly transferred into cell culture solution IV and cultured for 2 days; directly transferred into cell culture solution V and cultured for 1 day; directly transferred into cell culture solution VI and cultured for 3 days; directly transferred into cell culture solution VII and cultured for 4 days; directly transferred into cell culture solution VIII and cultured for 4-6 days; directly transferred into cell culture solution IX and cultured for 4-6 days to obtain pancreatic endoderm cells.

The expression of several marker transcription factors related to pancreatic endoderm in cell populations at this stage was detected by immunofluorescent staining.

The antibody for detecting NKX2.2 was a murine-derived monoclonal antibody (commercially available from DSHB, Catalog No. 74.5A5); the antibody for detecting PDX1 was a goat-derived polyclonal antibody (commercially available from R&D Systems, Catalog No. AF2419); the antibody for detecting EGFP was chicken-derived polyclonal antibody (commercially available from Abcam, Catalog No. AB13970); the antibody for detecting NGN3 was sheep-derived polyclonal antibody (commercially available from R & D System, Catalog No. AF3444).

All antibodies were non-directly labeled antibody. In the assay, the following antibodies commercially available from Jackson ImmunoResearch were used for counterstaining: Alexa Fluor 488-labeled donkey-derived anti-goat polyclonal antibody (Catalog No. 705-545-147); Cyanine Cy3-labeled donkey-derived anti-goat polyclonal antibody (Catalog No. 705-165-147); Cyanine Cy3-labeled donkey-derived anti-sheep polyclonal antibody (Catalog No. 715-165-147); Alexa Fluor 488-labeled donkey-derived anti-mouse polyclonal antibody (Catalog No. 715-545-151); Cyanine Cy3-labeled donkey-derived anti-mouse polyclonal antibody (Catalog No. 715-145-151); Alexa Fluor 488-labeled donkey-derived anti-chicken polyclonal antibodies (Catalog No. 703-545-155).

The results were shown in FIG. 1. In the cells obtained in this stage, some of the cells expressed PDX1, a marker protein of pancreatic precursor (FIG. 1A), the other cells expressed NGN3-EGFP, and there was almost not co-staining of the two (FIG. 1B); NGN3-EGFP+ cells expressed pancreatic endocrine progenitor cell marker transcription factor NGN3 or early stage endocrine cell-related proteins NKX2.2, CHROMOGRANIN A (CHGA), etc. (FIG. 1C and FIG. 1D); indicating that the obtained cells are pancreatic endodermal stage cells, in which there exist NGN3-EGFP-labeled pancreatic endocrine progenitor cells or nascent endocrine cells.

The above-mentioned culture solutions were formulated as follows:

The cell culture solution I was prepared by mixing Essential 8 medium and Y27632 to obtain cell culture solution I, wherein the ratio of Essential 8 medium and Y27632 was 1 ml: 10 μmol.

Cell culture solution II was Essential 8 medium.

The cell culture solution III was prepared by mixing DMEM/F12 medium, BSA, rmWnt3A and ActivinA to obtain cell culture solution III, wherein the ratio of DMEM/F12 medium, BSA, rmWnt3A and ActivinA was 1 ml: 0.1 g: 25 ng: 120 ng.

The cell culture solution IV was prepared by mixing DMEM/F12 medium, BSA and ActivinA to obtain cell culture solution IV, wherein the ratio of DMEM/F12 medium, BSA and ActivinA was 1 ml: 0.1 g: 120 ng.

The cell culture solution V was prepared by mixing DMEM/F12 medium, BSA, ActivinA and Wnt-059 to obtain cell culture solution V, wherein the ratio of DMEM/F12 medium, BSA, ActivinA and Wnt-059 was 1 ml: 0.1 g: 120 ng: 50 nmol.

The cell culture solution VI was prepared by mixing DMEM/F12 medium, B27 supplement without VitaminA, KGF and SB525334 to obtain cell culture solution VI, wherein the ratio of DMEM/F12 medium, B27 supplement without VitaminA, KGF and SB525334 was 1 ml: 10 μl: 50 ng: 1 μmol.

The cell culture solution VII was prepared by mixing DMEM-H medium, B27 supplement, all-trans retinoic acid, NOGGIN and SANT-1 to obtain cell culture solution VII, wherein DMEM-H medium, B27 supplement, all-trans Retinoic acid, NOGGIN and SANT-1: 1 ml: 10 μl: 2 μmol: 250 ng: 0.25 μmol.

The cell culture solution VIII was prepared by mixing DMEM-H medium, B27 supplement without VitaminA, NOGGIN and TPB ((2S, 5S)-(E, E)-8-(5-(4-trifluoromethyl)phenyl)-2,4-pentadienoylamino benzolactam) to obtain cell culture solution VIII, wherein the ratio of DMEM-H medium, B27 supplement without VitaminA, NOGGIN and TPB is 1 ml: 10 μl: 250 ng: 50 nmol.

The cell culture solution IX was prepared by mixing DMEM-H medium, B27 supplement without VitaminA, NOGGIN, human LIF and Alk5 inhibitor II to obtain cell culture solution VIII, wherein the ratio of DMEM-H medium, B27 supplement without VitaminA, NOGGIN and TPB is 1 ml: 10 μl: 250 ng: 10 ng: 1 μmol.

1.2 Flow Cytometry Analysis was Used to Identify Whether NGN3-EGFP+ Cells were Pancreatic Endocrine Progenitor Cells or Nascent Endocrine Cells.

The pancreatic endoderm cells obtained as described above were subjected to flow cytometry analysis with BD FACS Aria IIu to obtain two cell populations, NGN3-EGFP+(cell population containing pancreatic endocrine precursor origin) and NGN3-EGFP− (cell population not containing pancreatic endocrine precursor origin). EGFP is FL1 channel.

The presence of multiple marker transcription factors or secretory proteins of pancreatic endocrine progenitor cells in the NGN3-EGFP+ and NGN3-EGFP− populations was detected by intracellular flow cytometry analysis.

Antibody for detecting NKX2.2 was a murine-derived monoclonal antibody (commercially available from DSHB, Catalog No. 74.5A5); antibodies for detecting NGN3 included a sheep-derived polyclonal antibody (commercially available from R&D Systems, Catalog No. AF3444) and a mouse-derived monoclonal antibody (commercially available from DSHB, Catalog No. F25A1B3); antibody for detecting NEUROD1 was a goat-derived polyclonal antibody (commercially available from R&D Systems, Catalog No. AF2746); antibody for detecting PDX1 was goat-derived polyclonal antibody (commercially available from R & D Systems, Catalog No. AF2419); and antibody for detecting CHROMOGRANIN A was a rabbit-derived polyclonal antibody (commercially available from Catalog No. ZA-0507).

All antibodies were non-directly labeled antibody. In the assay, the following antibodies commercially available from Jackson ImmunoResearch were used for counterstaining: Alexa Fluor 488-labeled donkey-derived anti-goat polyclonal antibody (Catalog No. 705-545-147); Alexa Fluor 488-labeled donkey-derived anti-mouse polyclonal antibody (Catalog No. 715-545-151), Alexa Fluor 647-labeled donkey-derived anti-mouse polyclonal antibody (Catalog No. 715-605-151); Alexa Fluor 488-labeled goat-derived anti-mouse antigen subtype 1 polyclonal antibody (Catalog No. 115-545-205); Alexa Fluor 647-labeled goat-derived anti-mouse polyclonal antibody (Catalog No. 115-605-205); Alexa Fluor 488-labeled goat-derived anti-mouse antigen subtype 2b polyclonal antibody (Catalog No. 115-545-207), Alexa Fluor 647-labeled goat-derived anti-mouse antigen subtype 2b polyclonal antibody (Catalog No. 115-605-207); Alexa Fluor 488-labeled donkey-derived anti-rabbit polyclonal antibody (Catalog No. 711-545-152).

Figure 2:
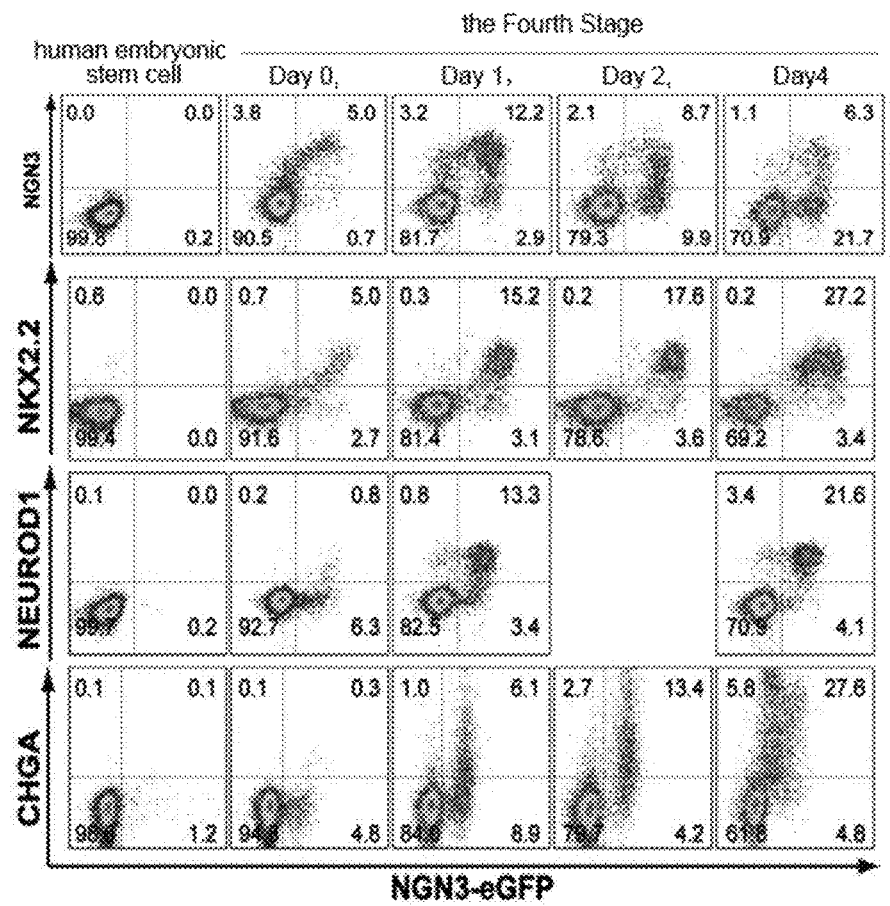
FIG. 2 shows the results of flow cytometry for identifying that NGN3-EGFP+ cells in pancreatic endoderm are pancreatic endocrine precursor cells or nascent endocrine cells. (a) Flow cytometry is used to detect the expression of NGN3-EGFP and pancreatic endocrine-related proteins such as NGN3, NKX2.2, NEUROD1, CHROMOGRANIN A (CHGA) in the pancreatic endoderm cells; (b) flow cytometry is used to detect the expressions of NGN3-EGFP and pancreatic precursor cell marker protein PDX1 in pancreatic endoderm cells, indicating that pancreatic precursor-related protein PDX1 is low expressed or not expressed in NGN3-EGFP+ cells.
Figure 2:
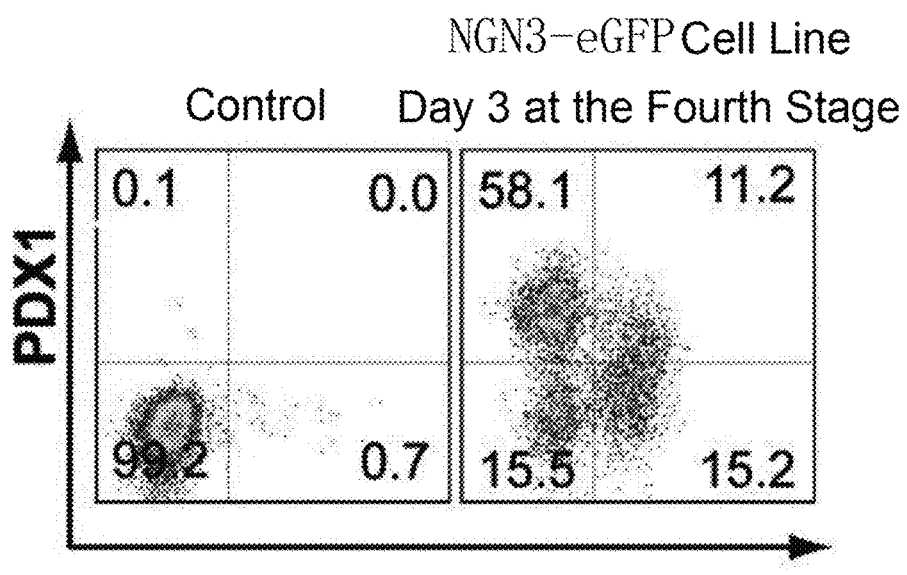

Results were shown in FIG. 2. NKX2.2, NGN3, and CHROMOGRANIN A (CHGA) were expressed in NGN3-EGFP+(containing pancreatic endocrine progenitor cells or nascent endocrine cells) population, but the pancreatic precursor-related gene PDX1 was not expressed or was low expressed therein, indicating that this cell population indeed mainly contains pancreatic endocrine progenitor cells or nascent endocrine cells.

There was no expression of NKX2.2, CHROMOGRANIN A (CHGA) and GFP in the NGN3-EGFP-population, which mainly highly expressed pancreatic precursor-related transcription factor PDX1 with a very small number of cells expressing NGN3 or NEUROD1, indicating that the cell population predominantly contains pancreatic progenitor cells or non-pancreatic cell type of cells.

1.3 NGN3-EGFP+ Cell Population was Enriched with Expression of SUSD2

1) RNA Sequencing Showed that the Expression of SUSD2 was Enriched in NGN3-EGFP+ Cell Population The NGN3-EGFP+ cells and the NGN3-EGFP-cells obtained in the above 2 were each extracted with RNeayPlus Mini Kit from QIAGEN to obtain 2 μg of total mRNA. The obtained mRNA was purified and subjected to reverse transcription to obtain single-stranded cDNA. 3'end of the resulting single-stranded cDNA was added with a polyA tail using terminal deoxynucleotidyltransferase. After amplification of the cDNA for 12 PCR cycles, a cDNA library was constructed with Illumina Paired-End DNA Sample Prep Kit, and then sequenced by Illumina Hiseq2000. The raw reads and the human reference genome (NCBI Build 37, hg19) were aligned by using Tophat software, and a transcriptome was reconstructed after forward or reverse matching of the mapping reads and the reference database of NCBI (RefSeq Genes hg19). After calculating the expression abundance of all genes and normalizing them with RPKM, the following criteria were used to determine the significance of differential expression of a gene between NGN3-EGFP+ and NGN3-EGFP-cells: 1) fold change of expression is greater than 2 or less than 0.5; 2) P value is less than 0.05. A heat map package of R software was used to analyze the obtained data based on RPKM using log 10. GO analysis was performed using differential gene expression (DGE).

Figure 3:
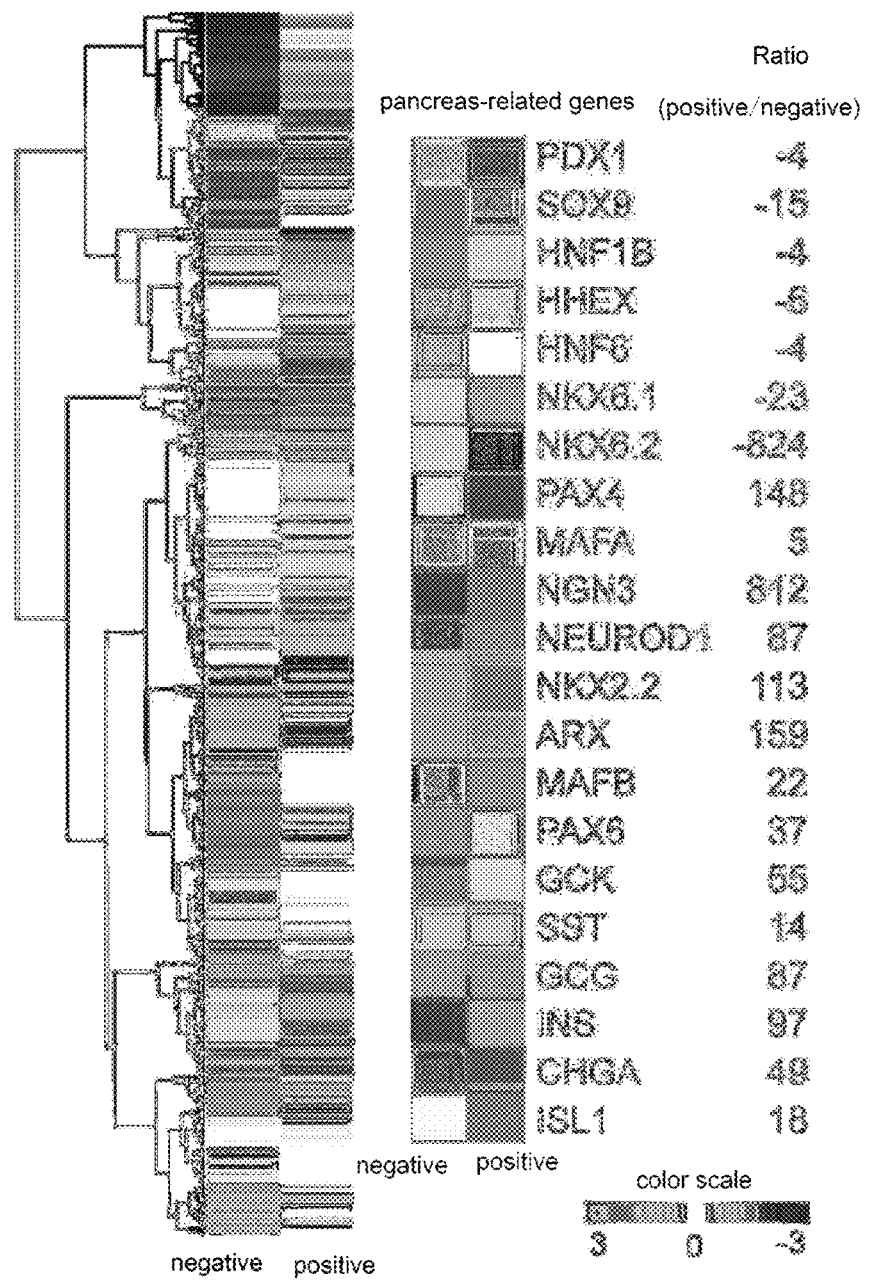
FIG. 3 shows the expression of pancreas-related genes in NGN3-EGFP+ cells and NGN3-EGFP-cells obtained by sorting with mRNA sequencing analysis, indicating that the population of pancreatic endocrine precursor cells and nascent endocrine cells of NGN3-EGFP+ are relatively enriched with the expression of pancreatic endocrine-related genes.

The results were shown in FIG. 3. Compared with NGN3-EGFP-cells, the expression of pancreatic endocrine-related genes NGN3, NEUROD1, NKX2.2, PAX4, ARX and the like was enriched in NGN3-EGFP+ cells, while the expression of pancreatic endocrine-related genes PDX1, HNF1B and HNF6 was low therein, indicating that the NGN3-EGFP+ cells obtained by sorting are pancreatic endocrine progenitor cells and nascent endocrine cells.

The expression of SUSD2 (NR02212) was enriched in NGN3-EGFP+ cells and the fold change was 2.30, indicating that the SUSD2 gene (SEQ ID NO: 2) can be used as a marker to identify whether the cell to be tested is a pancreatic endocrine progenitor cell or a nascent pancreatic endocrine cell. The next step is to identify whether the protein expressed by SUSD2 gene is in the same way.

(2) Immunofluorescence Antibody Method was Used to Demonstrate that SUSD2 could Mark NGN3-EGFP+ Cell Population Expression of EGFP and SUSD2 in NGN3-EGFP+ cells and NGN3-EGFP-cells obtained in above 2 was detected by immunofluorescent antibody method.

Antibody for detecting EGFP is a chicken-derived polyclonal antibody (commercially available from Abcam, Catalog No. AB13970); antibody for detecting SUSD2 is a murine-derived monoclonal antibody (commercially available from BioLegend, Catalog No. 327401).

All antibodies were non-directly labeled antibody. In the assay, the following antibodies commercially available from Jackson ImmunoResearch were used for counterstaining: Cyanine Cy3-labeled donkey-derived anti-mouse polyclonal antibody (Catalog No. 715-165-151); Alexa Fluor 488-labeled donkey-derived anti-chicken polyclonal antibody (Catalog No. 703-545-155).

Figure 4:
FIG. 4 shows immunofluorescent staining for detecting the merged staining pattern of SUSD2 and NGN3-EGFP, indicating that SUSD2 can be used to mark NGN3-EGFP+ cells derived from human pluripotent stem cells.

The results were shown in FIG. 4. The results of immunohistochemistry showed that the expression of SUSD2 was consistent with that of NGN3-EGFP and SUSD2 was not expressed in NGN3-EGFP-cells, i.e. the expression of SUSD2 was enriched in NGN3-EGFP+ cells; indicating that SUSD2 could be used to identify or mark NGN3-EGFP+ cells, that is, a mixed cell population composed of pancreatic endocrine progenitor cells or nascent pancreatic endocrine cells.

2. SUSD2 as a Marker Gene of Pancreatic Endocrine Progenitor Cell Obtained by Differentiation of Human Pluripotent Stem Cell.

2.1 Acquisition of Pancreatic Endoderm Cell

The isolated human pluripotent stem cell line NGN3-EGFP was differentiated into pancreatic endoderm cells according to the method of 1.1.

2.2 the Expression of SUSD2 Gene and the Expression of Pancreatic Endocrine Progenitor Cells Marker Gene NKX2.2 and NEUROD1 were Detected by Flow Cytometry.

The pancreatic endoderm cells obtained in the above 2.1 were subjected to flow cytometry to detect the expression of the protein encoded by SUSD2 gene according to a cell immobilization/permeabilization kit commercially available from BD Biosciences (Catalog No. 554714). After immobilizing the pancreatic endoderm cells obtained in the above 2.1, the corresponding antibody and the direct-labeled SUSD2 antibody (mouse-derived PE-labeled anti-SUSD2 monoclonal antibody (commercially available from BioLegend, catalog No. 327406) and mouse-derived APC-labeled monoclonal antibody (commercially available from BioLegend, Catalog No. 327408)) were used. Mouse-derived unlabeled monoclonal antibody (commercially available from BioLegend, Catalog No. 327401) was used for staining, and then fluorescent secondary antibody was used for counterstaining Subsequently, an analysis was conducted by a flow sorter.

Antibody for detecting NKX2.2 was murine-derived monoclonal antibody (commercially available from DSHB, Catalog No. 74.5A5); antibodies for detecting NGN3 included sheep-derived polyclonal antibody (commercially available from R & D Systems, Catalog No. AF3444) and mouse-derived monoclonal antibody (commercially available from DSHB, Catalog No. F25A1B3); antibody for detecting NEUROD1 was goat-derived polyclonal antibody (commercially available from R & D Systems, Catalog No. AF2746); antibody for detecting PDX1 was goat-derived polyclonal antibody (commercially available from R & D Systems, Catalog No. AF2419); and antibody for detecting CHROMOGRANINA was rabbit-derived polyclonal antibody (commercially available from Zhong Shan Jinqiao, Catalog No. ZA-0507).

The secondary antibodies were commercially available from Jackson ImmunoResearch: Alexa Fluor 488-labeled donkey-derived anti-goat polyclonal antibody (Catalog No. 705-545-147); Alexa Fluor 488-labeled goat-derived anti-mouse antigen subtype 2b polyclonal antibody (Catalog No. 115-545-207), Alexa Fluor 647-labeled goat-derived anti-mouse antigen subtype 2b polyclonal antibody (Catalog No. 115-605-207); Alexa Fluor 488-labeled donkey-derived anti-rabbit polyclonal antibody (Catalog No. 711-545-152); Alexa Fluor 488-labeled donkey-derived anti-chicken polyclonal antibody (Catalog No. 703-545-155).

Figure 5:
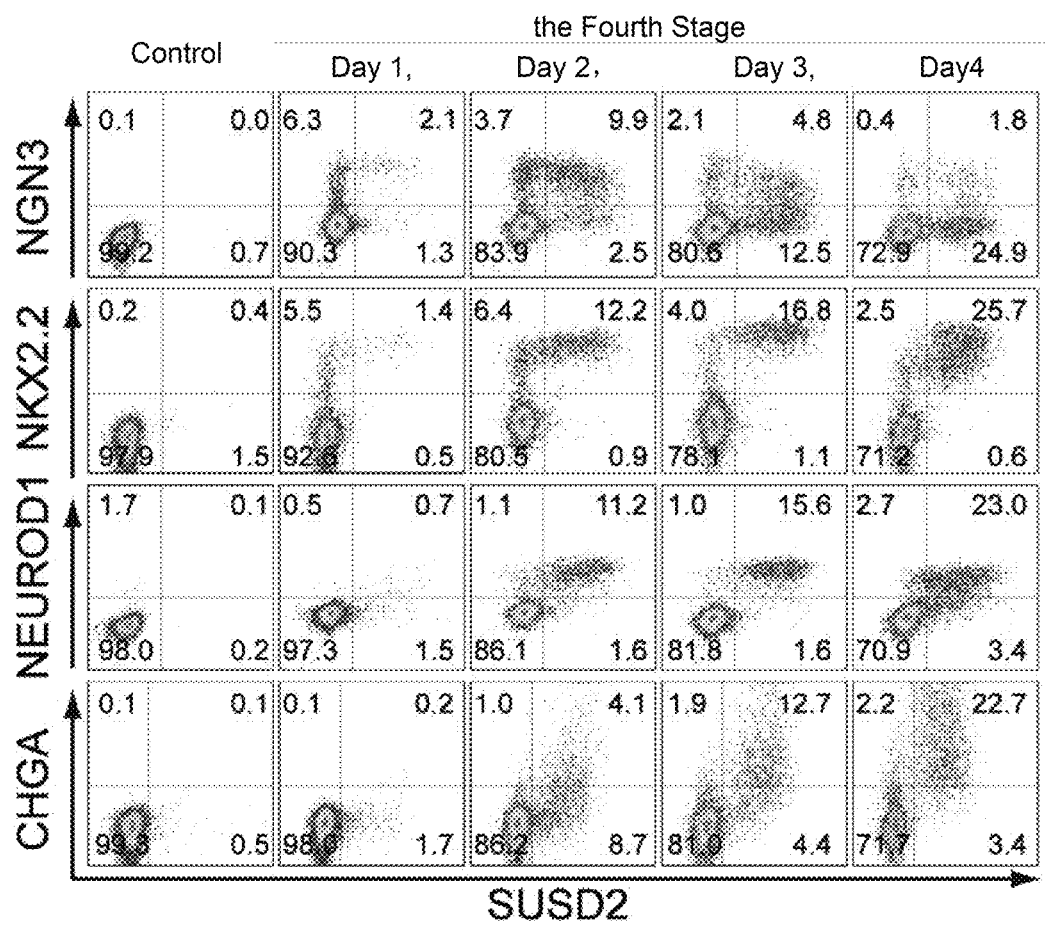
FIG. 5 shows an analysis graph of a flow cytometry for detecting the expression of SUSD2 and pancreatic development-related proteins in pancreatic endoderm cells derived from human pluripotent stem cells, indicating that SUSD2 can be used to mark pancreatic endocrine precursor cells and nascent endocrine cells obtained by differentiation in vitro. (a) Flow cytometry is used to detect the expression of SUSD2 and pancreatic endocrine-related proteins such as NGN3, NKX2.2, NEUROD1, CHROMOGRANIN A (CHGA) in pancreatic endoderm cells; (b) flow cytometry is used to detect the expression of SUSD2 and pancreatic precursor cell-related proteins PDX1 in pancreatic endoderm cells.
Figure 5:
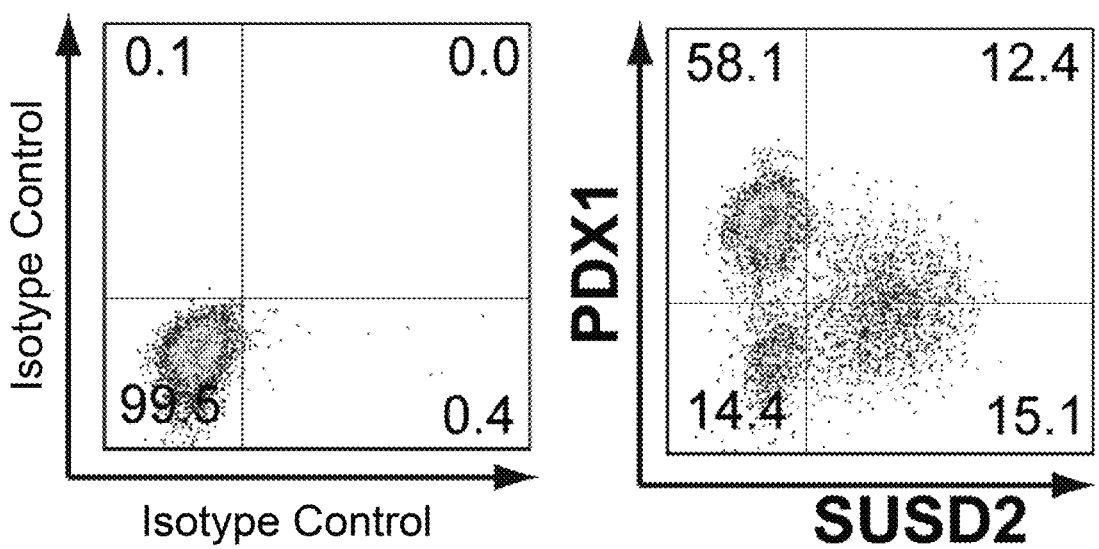

As shown in FIG. 5, NGN3 positive or weakly positive cells did not express SUSD2 or NEUROD1 and weakly expressed NKX2.2 on day 0 of the fourth stage. On day 1 of the fourth stage, 80%, 93% and 88% of SUSD2+ cells expressed NGN3, NKX2.2 and NEUROD1, respectively. This indicates that most of SUSD2+ cells express NGN3, NKX2.2 and NEUROD1 simultaneously, indicating that this population of SUSD2+ cells has the characteristics of endocrine progenitor cell. On day 4 of the fourth stage, most of the SUSD2+ cells expressed NKX2.2 or CHROMOGRANIN A (CHGA) but did not express NGN3, indicating that this population of SUSD2+/NGN3– cells had the characteristics of endocrine cell during this period. In addition, SUSD2+ cells weakly expressed or did not express PDX1, the marker of pancreatic precursors, sustainedly, indicating that SUSD2 could be used to mark pancreatic endocrine progenitor cells and their progeny endocrine cells.

In the whole differentiation process, although part of SUSD2 cells express pancreatic endocrine-related proteins NGN3, NKX2.2 and the like, most SUSD2-cells do not express these pancreatic endocrine-related proteins but express pancreatic precursor-related protein PDX1, indicating that SUSD2-cells mainly contain pancreatic progenitor cells or non-pancreatic cell type of cells (FIG. 5).

These results indicate that SUSD2+ cells are pancreatic endocrine progenitor cells or nascent pancreatic endocrine cells, further demonstrating that expression of the protein encoded by SUSD2 gene can be used to identify whether the cells are target cells.

2.3 Detection of SUSD2+ cells at mRNA level showed that SUSD2-cells and SUSD2+ cells were obtained by flow sorting, and the gene expression profiles of these two populations of cells and unsorted pancreatic endoderm cells were analyzed by quantitative PCR. Power SYBR® Master Mix kit was used for quantitative PCR (commercially available from Life Technologies, Catalog No. 4367659). The primers used in the amplification were shown in Table 1 and the internal reference primer was GAPDH. See the instructions for specific operations.

Table 1 Shows Amplification Primers

| Gene | 5'-primer | 3'-primer |
|---|---|---|
| HHEX | ACCTCTACTCTGGAGCCCCTTCT | ATCTCACCTGGCCGCCTTT |
| WNT3 | ACAAGCACAACAACGAGGCG | GAGGTGCATGTGGTCCAGGATAG |
| MIXL1 | CCGAGTCCAGGATCCAGGTA | CTCTGACGCCGAGACTTGG |
| MEOX1 | GCGATGACTACGGGGTGCTT | TTCTCCGCCTGGATGATTTC |
| GAPDH | TGCACCACCAACTGCTTAGC | GGCATGGACTGTGGTCATGAG |
| OCT4 | CCGAAAGAGAAAGCGAACCAG | ATGTGGCTGATCTGCTGCAGT |
| SOX17 | GCATGACTCCGGTGTGAATCT | TCACACGTCAGGATAGTTGCAGT |
| T | GATGATCGTGACCAAGAACGG | CCACGAAGTCCAGCAGGAA |
| FOXA2 | CTGAGCGAGATCTACCAGTGGA | CAGTCGTTGAAGGAGAGCGAGT |
| CXCR4 | CCATCGTCCACGCCACCAAC | ACGCCAACATAGACCACCTT |
| CER1 | TGAAGTACATTGGGAGACCTGC | CACAGCCTTCGTGGGTTATAGT |
| BRAX1 | CACGCCGGACAGAATAGATC | GGTACCACGTCTTCACCTGCAAC |
| CDX2 | CTGGAGCTGGAGAAGGAGTTTC | ATTTTAACCTGCCTCTCAGAGAGC |
| AFP | CCCGAACTTTCCAAGCCATA | TACATGGGCCACATCCAGG |
| SOX2 | CCATGACCAGCTCGCAGAC | GGACTTGACCACCGAACCC |
| HNF1B | GCACCTCTCCCAGCATCTCA | GTCGGAGGATCTCTCGTTGC |
| HNF4A | ACTACATCAACGACCGCCAGT | ATCTGCTCGATCATCTGCCAG |
| HNF6 | TGTGGAAGTGGCTGCAGGA | TGTGAAGACCAACCTGGGCT |
| HB9 | GCTCATGCTCACCGAGACCC | TTTGCTGCGTTTCCATTTCATC |
| NKX61 | GGGCTCGTTTGGCCTATTCGTT | CCACTTGGTCCGGCGGTTCT |
| PDX1 | CGGAACTTTCTATTTAGGATGTGG | AAGATGTGAAGGTCATACTGGCTC |
| CAP1 | CTCGGAAGATTTGGCACTGACTAT | CGTGGTGGGCATTGTGGAGATA |
| PTF1A | GAAGGTCATCATCTGCCATCG | GGCCATAATCAGGGTCGCT |
| SOX9 | CTGAGCTCGGCGTTGTG | AAAGGCTACGACTGGACG |
| NOD1 | ATTGCACCAGCCCTTCCTTTGAT | ACTCGGCGGACGGTTCGTTTT |
| NGN3 | GGCTGTGGGTGCTAAGGGTAAG | CAGGGAGAAGCAGAAGGAACAA |
| NKX22 | TTCAGAACCACCGCTACAAG | GGGCGTCACCTCCATACCT |
| PAX6 | CGAATTCTGCAGGTGTCCAA | ACAGACCCCCTCGGACAGTAAT |
| ARX | GGAGGCAGAAAGGCACAAAGA | GGTGGGGTTAGATAGCGGGTT |
| PAX4 | AGTGTCTCCTCCATCAACCG | TGGTGACCTGAGCCGTGT |
| AMY | AGGAGGTAATTGATCTGGGTGG | AAGTGCTCTGTCAGAAGGCATG |
| GCG | GAGATTTCCCAGAAGAGGTCG | TGGCGGCAAGATTATCAAGAA |
| GCK | CTTCCCTCAGTTTTTCGGTGG | TTGATTCCAGCGAGAAAGGTG |
| INS | GCAGCCTTTGTGAACCAACAC | CCCCGCACACTAGGTAGAGA |
| ISL1 | ATTTCCCTATGTGTTGGTGCG | CGTTCTTGCTGAAGCCGATG |
| MAFB | CCCGACCGAACAGAAGACA | ACTGGGTGCGAGCCGATGAG |
| SST | CGCTGTCCATCGTCCTG | GGGCATCATTCTCCGTCTG |
| GRELIN | GAGGCCCCAGCCGACAAGTG | AAGCAAGCGAAAAGCCAGAT |
| PPY | AGTGTACCCAGGGGACAATGC | CAGCATGTTGATGTATCTACGGA |
| MAFA | CAGAGCCAGGTGGAGCAGC | CGTATTTCTCCTTGTACAGGTCCC |
| CELA2A | CATCGTCAGCTTCGGGTCTCGC | GAAGACGGAGGGCTTGTGGTAG |
| CTRB1 | CGCCATCCACCCTGTGCTCA | GACGGCGTCCTCCCCATTCA |
| CPA1V2 | CCTGGGCTGGGTGGCTATGG | GCGGCATCATTCATTTCTTTCA |
| CHROMO-GRANINA (CHGA) | CGCAAACCGCAGACCAGAGGA | AGCTCTGCTTCAATGGCCGACA |
| SUSD2 | GGCACCGCCAACACCTCA | GCGTGGGCAGCGACTTGA |

Figure 6:
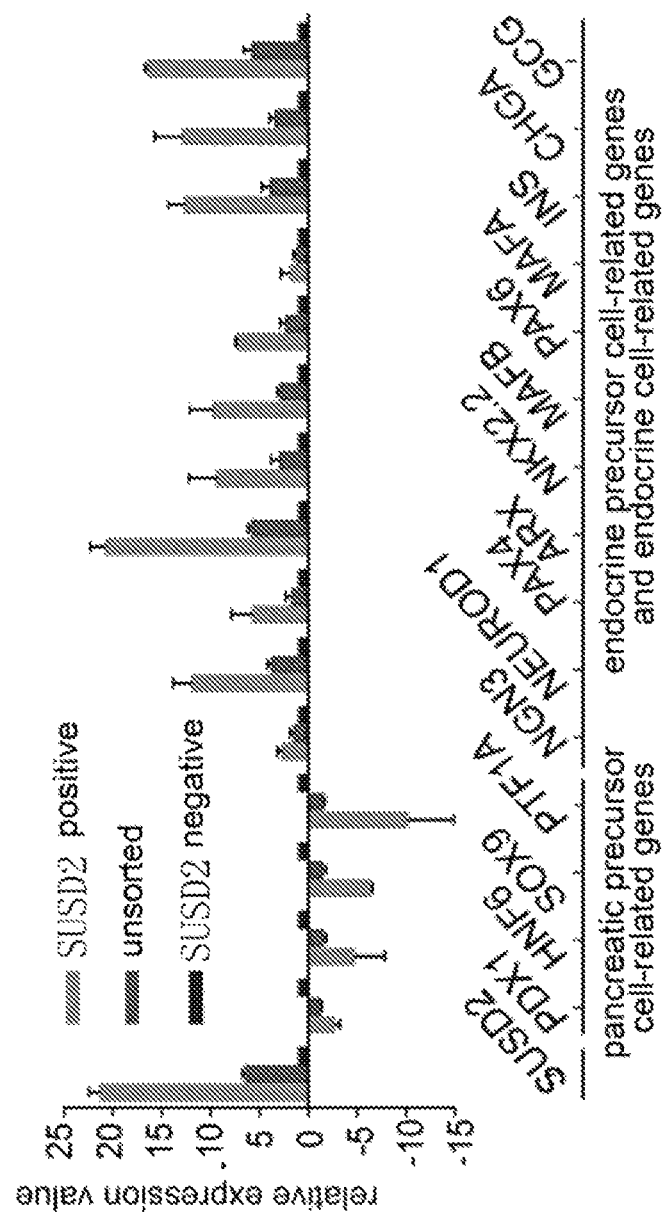
FIG. 6 shows the expression of pancreatic development-related genes in SUSD2+ cells, SUSD2-cells obtained by sorting with flow cytometry and in unsorted pancreatic endoderm cells identified by RT-QPCR, indicating that SUSD2+ cells are relatively enriched with the expression of pancreatic endocrine precursor cell-related genes and pancreatic endocrine cell-related genes and relatively weakly express the pancreatic precursor cell-related genes, demonstrating that cells labeled by SUSD2 are pancreatic endocrine precursor cells and/or nascent endocrine cells.

The results were shown in FIG. 6. The expression of genes NGN3, NEUROD1, NKX2.2, PAX4, ARX and the like related to pancreatic endocrine progenitor cells and endocrine cells was enriched in SUSD2+ cells, indicating that they were pancreatic endocrine progenitor cells or nascent endocrine cells, while the expression of PDX1, HNF6, SOX9, PTF1A and the like related to pancreatic precursors was enriched in SUSD2 cells, indicating that they were not pancreatic endocrine progenitor cells or new endocrine cells.

3. SUSD2-Positive Cells and SUSD2-Negative Cells were Sorted by Magnetic Beads 3.1 Acquisition of Pancreatic Endoderm Cell The isolated human pluripotent stem cell line H1 was differentiated into pancreatic endoderm cells according to the method of 1.1.

3.2. Magnetic Beads Cell Sorting

The pancreatic endoderm cells were subjected to magnetic beads cell sorting, wherein the required antibody is the directly labeled SUSD2 antibody (mouse-derived PE-labeled anti-SUSD2 monoclonal antibody was commercially available from BioLegend, Catalog No. 327406), the magnetic cell sorting-related reagents were commercially available from MiltenyiBiotec, and the SUSD2-positive cells and SUSD2-negative cells were obtained according to the instructions for use.

3.3. Detection

A. Flow Cytometry Analysis

SUSD2+ cells, SUSD2-cells and unsorted cells were analyzed by flow cytometry as described above.

Figure 7A:
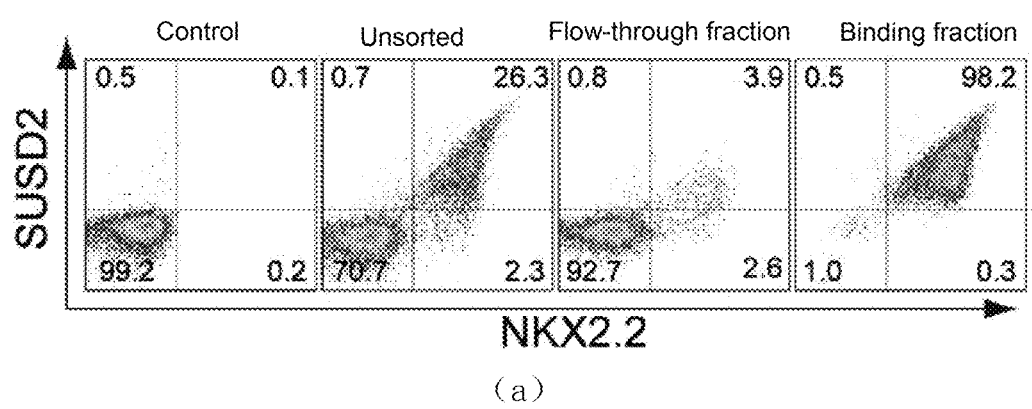
FIG. 7 shows the SUSD2 antibody is used in magnetic cell sorting to enrich pancreatic endocrine precursor cells and nascent pancreatic endocrine cells. (a) The expression of NKX2.2 marker protein of pancreatic endocrine precursor cells and pancreatic endocrine cells in SUSD2+ cells and SUSD2-cells enriched by performing magnetic cell sorting on pancreatic endoderm cells obtained by differentiation in vitro with SUSD2 antibody is detected by flow cytometry, indicating that the use of SUSD2 antibody in magnetic cell sorting can efficiently enrich NKX2.2+ pancreatic endocrine precursor cells and nascent pancreatic endocrine cells. (b) After SUSD2+ cells and SUSD2-cells obtained by magnetic cell sorting and unsorted pancreatic endoderm cells are subjected to extended culture, the expression of pancreatic precursor- and pancreatic endocrine-related proteins is detected by immunohistochemistry, indicating that SUSD2+ cells can produce a large number of endocrine cells which are proved to be endocrine precursor cells or nascent endocrine cells. (c) SUSD2+ cells and SUSD2-cells obtained by magnetic cell sorting are transplanted into the immunodeficient mice. After 19 weeks, an immunofluorescent staining of the implants is carried out to detect the expression of pancreatic endocrine-related protein, indicating that SUSD2+ cells are able to produce multiple types of pancreatic endocrine cells, while SUSD2-cells mainly produce duct-like cells, demonstrating that the cells enriched by SUSD2 are pancreatic endocrine precursor cells or nascent pancreatic endocrine cells.

The results were shown in FIG. 7(a). SUSD2+ cells were able to enrich NKX2.2+ cells with high purity, which were NGN3+ endocrine progenitor cells or nascent endocrine cells (FIG. 7(a)).

B) Progeny cells obtained by culturing SUSD2-positive cells were identified by immunofluorescence. The SUSD2+ cells and SUSD2-cells obtained by sorting and the unsorted pancreatic endoderm cells were subjected to extended culture in vitro. The target cells were resuspended in cell culture solution X and plated on Matrigel-coated cell culture plates for one day to adhere. The next day, the medium was removed and the cells were washed with PBS. Cells were cultured for another 5 days in cell culture solution XI. The culture conditions were 37° C. and 5% $CO_2$.

The cell culture solution X was obtained by the following method: DMEM-H: B27 without VitaminA: Y27632=1 ml: 10 μl: 10 μM.

The cell culture solution XI was obtained by the following method: DMEM-H: B27 without vitamin A: Noggin: human LIF: Alk5 inhibitor II=1 ml: 10 μl: 250 ng: 10 ng: 100 nM.

Immunohistochemical staining was conducted.

Figure 7B:
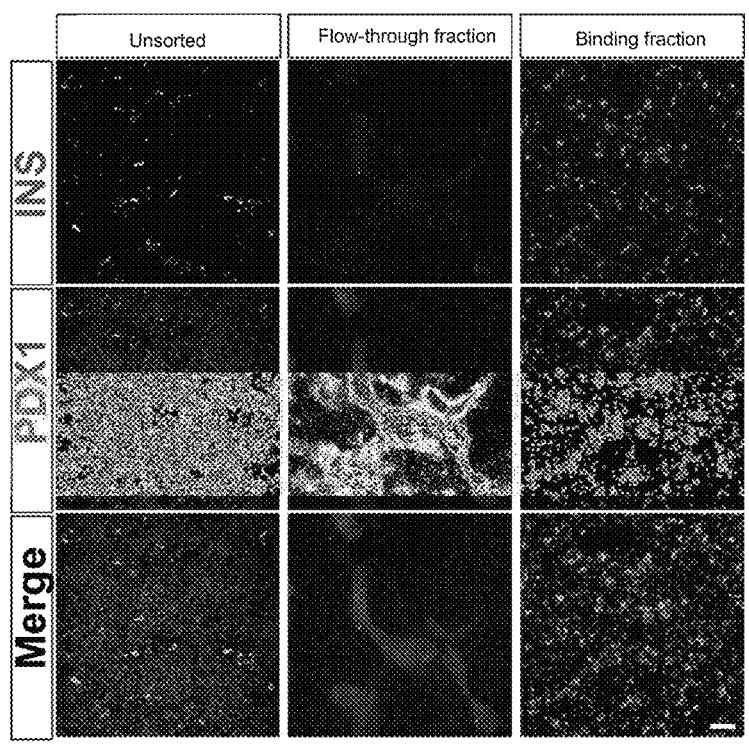

The results were shown in FIG. 7(b). Cells obtained by culturing SUSD2+ cells were able to produce a large amount of INSULIN+ cells, i.e. a large number of endocrine cells were obtained. The cells obtained by culturing SUSD2– cells were mainly PDX1+ pancreatic progenitor cells and were capable of producing only a small amount of INSULIN+ cells, indicating that cells enriched by SUSD2 were pancreatic endocrine precursor cells.

It is indicated that the cells enriched by SUSD2 are pancreatic endocrine precursor cells or nascent endocrine cells.

C) Transplantation into Renal Cysts of Immunodeficient Mouse

The transplantation of renal cysts into immunodeficient mouse (6-8 weeks) was performed by implanting SUSD2-positive cells and SUSD2-negative cells obtained by sorting as well as unsorted pancreatic endoderm cells. After 19 weeks of transplantation, the implants were harvested and frozen sections were prepared for immunohistochemical staining.

Figure 7C:
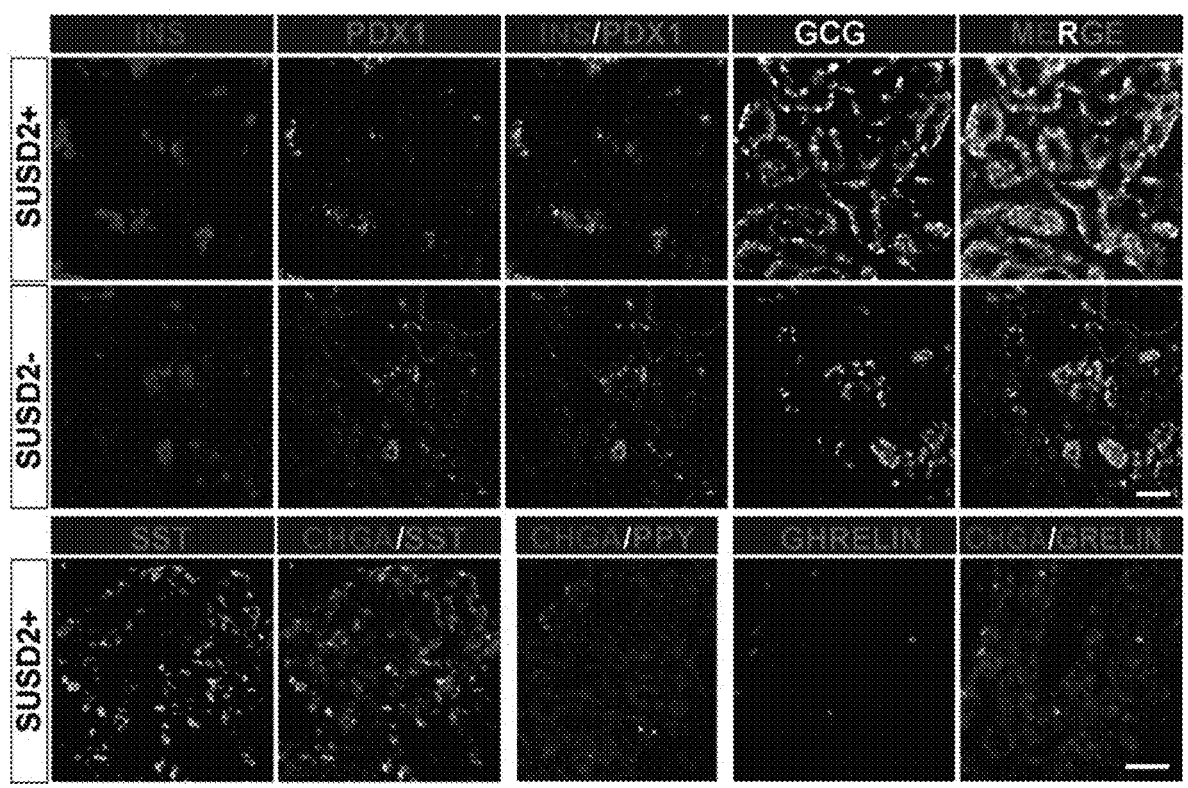

The results were shown in FIG. 7(c). SUSD2+ and SUSD2– cells obtained by MACS were transplanted into mice, and as a result, SUSD2+ cells were able to produce all kinds of endocrine cells (INSULIN+ beta-cells, Glucagon+ alpha cells, SST+ delta cells, Ghrelin+ epsilon cells, and PPY+ PPY cells), while no duct-like structure was produced, indicating that SUSD2+ cells are pancreatic endocrine precursor cells or nascent endocrine cells.

4. SUSD2 Used for In Vivo Sorting of Human Embryonic-Derived Pancreatic Endocrine Precursor Cells and Nascent Endocrine Cells.

4.1 Immunofluorescence Staining of Frozen Section of Human Embryonic Pancreatic Tissue Tissue sectioning: isolated human fetal pancreatic tissue was fixed with 4% PFA at 4° C. for 2 hours and washed three times with PBS at 4° C. for a moment, 10 minutes and 2 hours, respectively, followed by placing the tissue masses in 30% sucrose solution at 4° C. overnight until the tissue was settled. The resulting tissue masses were embedded in Optimal Cutting Temperature Compound (O.C.T) (Tissue-Tek), frozen in liquid nitrogen, sliced into 10 μm sections by freezing microtomeCryostat (Leica).

Figure 8A:
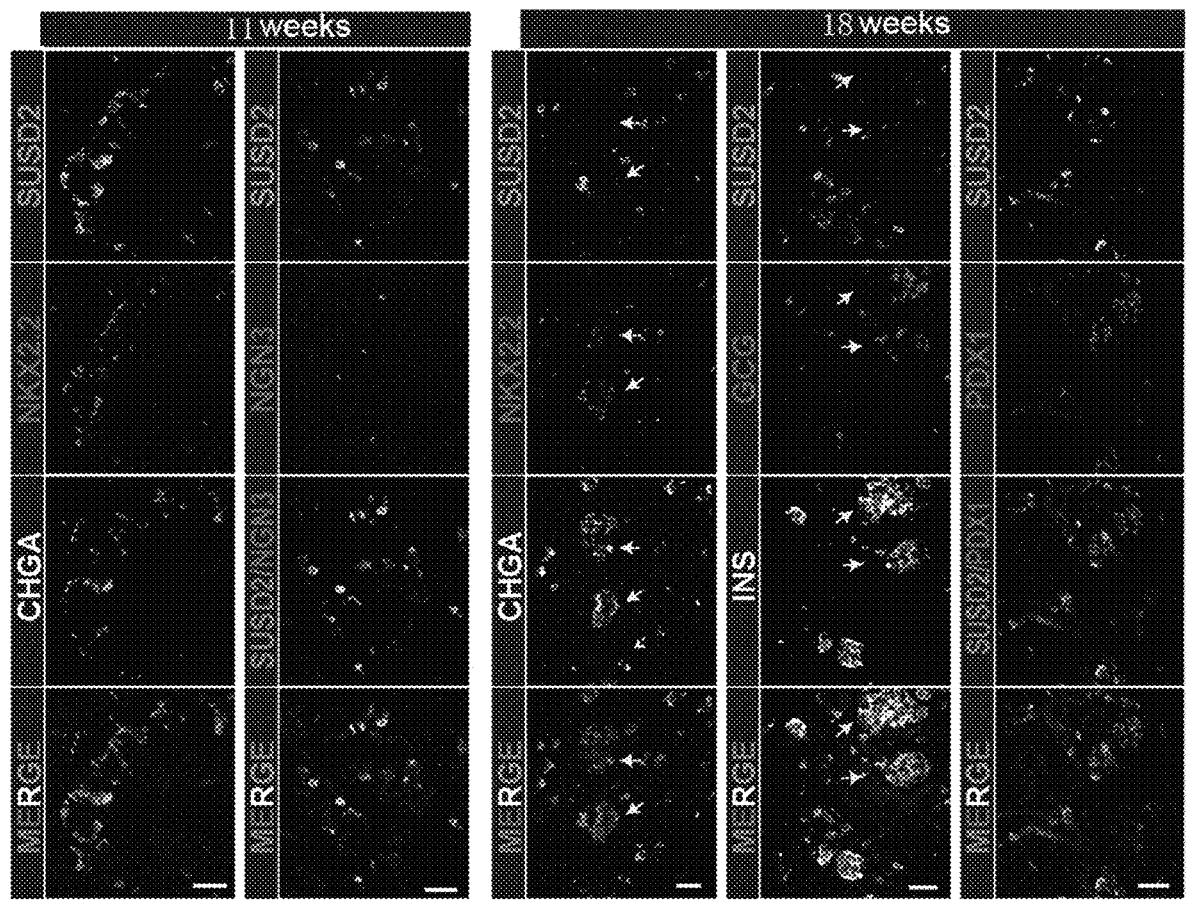
FIG. 8 shows that SUSD2 can be used to mark pancreatic endocrine precursor cells and nascent pancreatic endocrine cells derived from human embryos. (a) Co-expression of SUSD2 with pancreas endocrine progenitor cell-related proteins and pancreatic endocrine cell-related proteins in embryonic pancreas tissues and adult pancreas tissues is detected by immunohistochemistry, indicating that SUSD2 is only expressed in pancreatic endocrine precursors or endocrine cells in embryonic pancreas tissues. (b) The expression of SUSD2 and the pancreatic endocrine-related protein and pancreatic duct-related protein in the embryonic pancreas tissues is detected by immunofluorescence.
Figure 8B:
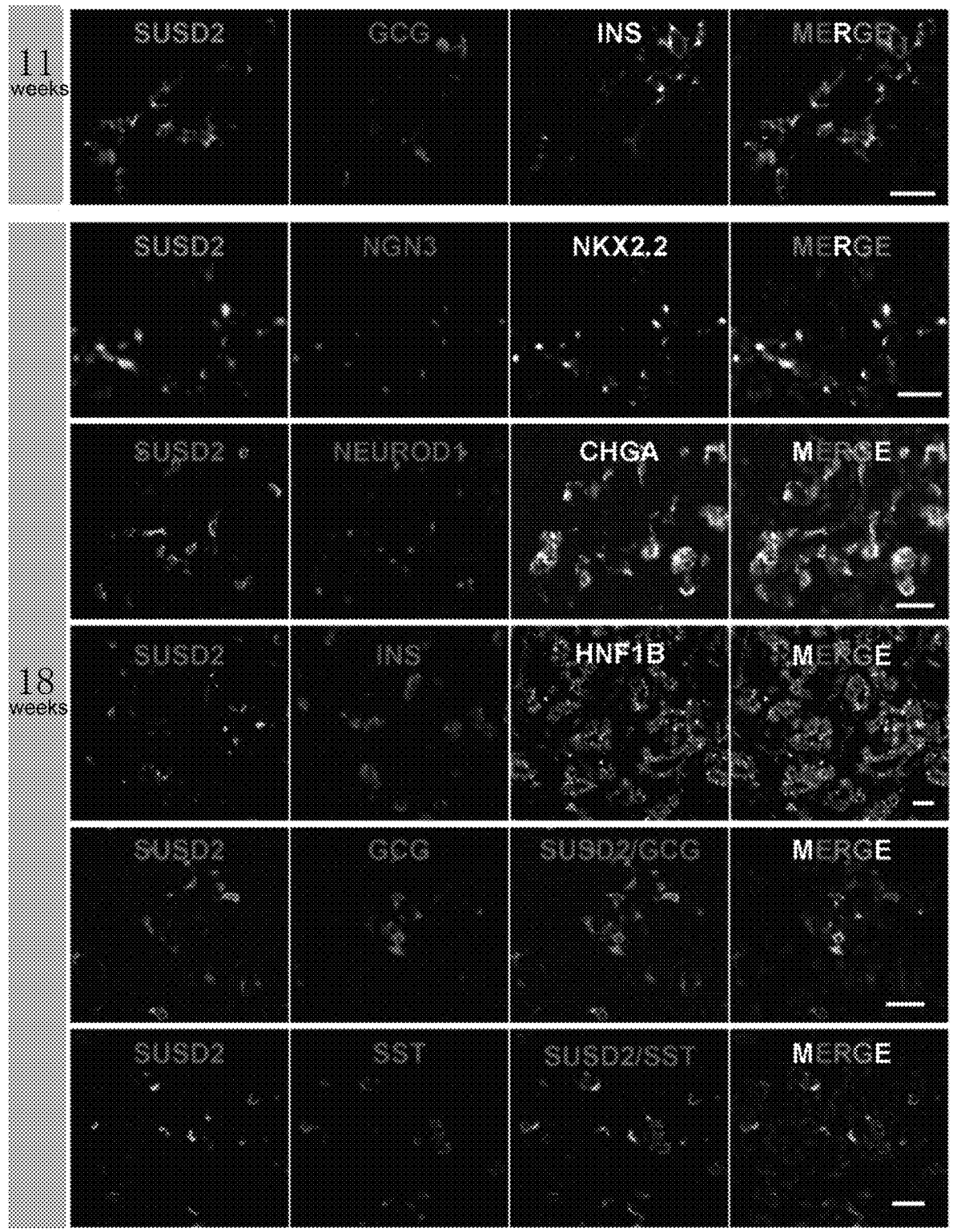

The resulting sections were detected by using immunofluorescent antibody assay according to 1.1, showing that the sections were cells of the pancreatic endoderm stage and the cells labeled by SUSD2 were pancreatic endocrine precursor cells and/or nascent pancreatic endocrine cells (FIG. 8).

4.2 Enrichment of Human Embryo Pancreas-Derived Endocrine Progenitor Cells and Nascent Endocrine Cells by Magnetic Cell Sorting The fetal pancreatic tissue was washed twice with cold PBS and cut into small pieces of 1 cubic mm with an ophthalmic shears. Then the pieces were digested with digestion solution (PRMI 1640, 100-400 U/ml Collagenase IV (Life Technologies), 1.2 U/ml Dispase II (Roche), DNase I (0.02%, (wt/vol)) and 0.5% fetal bovine serum (FBS, Hyclone) at 37° C. for 30 minutes, and the cells were dispersed by gentle pipetting with a pipette every 5 minutes. The digested single cells were transferred to PRMI 1640 with 0.5% FBS and washed twice with PBS containing 0.5% BSA and 2 mM EDTA. The remaining tissue masses were collected and digested again as described above. The resulting cell suspension was filtered through 40 μm cell sieve (BD Biosciences) and the resulting single cell suspension was stored in PBS containing 0.5% BSA and 2 mM EDTA and placed on ice for subsequent analysis.

The resulting single cell suspension was subjected to magnetic cell sorting, and the desired antibody was the directly labeled SUSD2 antibody (mouse-derived PE-labeled anti-SUSD2 monoclonal antibody, commercially available from BioLegend, catalog No. 327406) to obtain SUSD2-positive cells and SUSD2-negative cells.

4.3 The positive cells were identified as pancreatic endocrine progenitor cells or nascent endocrine cells by fluorescent quantitative PCR and SUSD2-positive cells and SUSD2-negative cells obtained by magnetic cell sorting and unsorted embryonic pancreas cells were quantified by quantitative PCR to detect the expression of genes related to pancreatic endoderm cells. For details, refer to 2.3.

Figure 9:
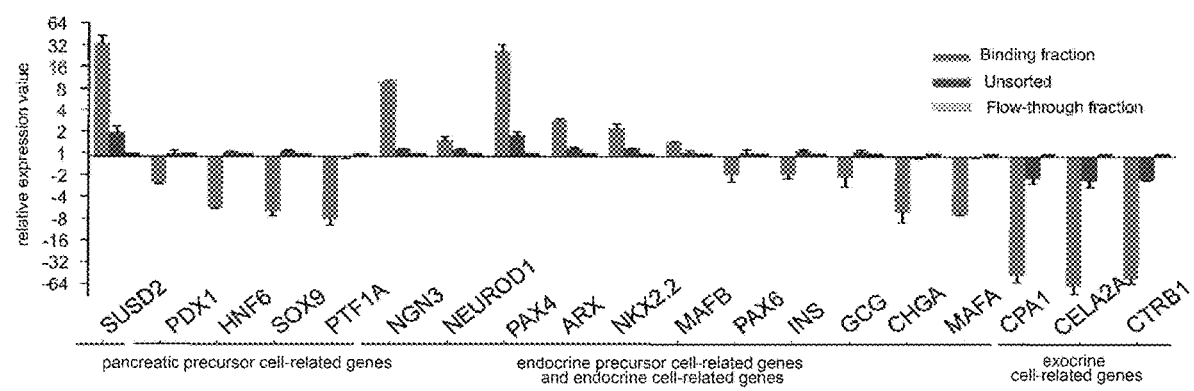
FIG. 9 shows that SUSD2 can be used to enrich pancreatic endocrine precursor cells and nascent pancreatic endocrine cells derived from human embryonic pancreas.

Results were shown in FIG. 9. SUSD2-positive cells were enriched with the expression of SUSD2 gene, and also with the expression of genes NGN3, NEUROD1, NKX2.2, PAX4, ARX and so on related to pancreatic endocrine progenitor cells and early stage endocrine cells, they also weakly expressed pancreatic progenitor cell-related genes PDX1, HNF6, SOX9, PTF1A, late phase endocrine cell-related genes INSULIN, GLUCAGON, PAX6, MAFB, MAFA, CHROMOGRANIN A (CHGA) and exocrine cell-related gene CPA1 and the like, indicating that SUSD2-positive cells are pancreatic endocrine progenitor cells or nascent endocrine cells.

Therefore, it can be seen that pancreatic endocrine progenitor cells or nascent pancreatic endocrine cells in a population of cells to be tested can be sorted or assisted in sorting by detecting whether the SUSD2 gene used as a marker gene of pancreatic endocrine progenitor cells or nascent endocrine cells expresses or not, the details of which are as follows:

The cells in the population of cells to be tested were tested for expression of the SUSD2 gene, and if some cells express the SUSD2 gene, these cells are or are candidates for human pancreatic endocrine progenitor cells or their progeny cells that do not secrete hormones; if some cells do not express SUSD2, these cells are not, or are not candidates for, human pancreatic endocrine progenitor cells or their nascent pancreatic endocrine cells.

The detection method is carried out by detecting whether the cells in the population of cells to be tested contain a protein expressed by the SUSD2 gene, specifically by detecting the expression of the SUSD2 gene at mRNA level or by detecting the protein expressed by the SUSD2 gene by a immunofluorescent antibody method or by detecting the protein expressed by the SUSD2 gene by flow cytometry or by sorting the protein expressed by the SUSD2 gene with magnetic beads.

Example 2 Human Pancreatic Endocrine Progenitor Cells or their Progenitor Cells that do not Secrete Hormones were Sorted by Detecting the Expression of the SUSD2 Gene 1. Pancreatic Endoderm Cells were Obtained The isolated human pluripotent stem cell line was differentiated into pancreatic endoderm cells according to the method of 1.1.

2. Flow Cytometry was Performed to Sort Human Pancreatic Endocrine Progenitor Cells or their Progenitor Cells that do not Secrete Hormones by Detecting the Expression of SUSD2 Gene Pancreatic endoderm cells were detected by flow cytometry using the directly labeled SUSD2 antibody (mouse-derived PE-labeled anti-SUSD2 monoclonal antibody, commercially available from BioLegend, catalog no. 327406). Specifically, the cells were subjected to staining with the antibody, followed by counterstaining with a Fluorescent secondary antibody.

If some cells express the SUSD2 gene, these cells are or are candidates for human pancreatic endocrine progenitor cells or their progeny cells that do not secrete hormones; if some cells do not express the SUSD2 gene, these cells are not or are not candidates for human pancreatic endocrine progenitor cells or their progeny cells that do not secrete hormones; SUSD2+ cells were selected as human pancreatic endocrine progenitor cells or nascent pancreatic endocrine cells.

Meanwhile, the expression of pancreatic endocrine progenitor cell marker genes NGN3, NKX2.2 and NEUROD1 was detected by flow cytometryin SUSD2+ cells. Antibody for detecting NKX2.2 was murine-derived monoclonal antibody (commercially available from DSHB, Catalog No. 74.5A5); antibodies for detecting NGN3 included sheep-derived polyclonal antibodies (the antibody was commercially available from R & D Systems, Catalog No. AF3444) and murine-derived monoclonal antibodies (the antibody was commercially available from DSHB, Catalog No. F25A1B3); antibody for detecting NEUROD1 was goat-derived polyclonal antibody (the antibody was commercially available from R & D Systems, Catalog No. AF2746).

Results show that SUSD2+ cells express the pancreatic endocrine precursor cell marker genes NGN3, NKX2.2 and NEUROD1, proving that they are indeed human pancreatic endocrine precursors or their progeny cells that do not secrete hormones. Thus, it is proved that the method of the present invention is applicable.

The invention claimed is:

1. A method of identification, screening or sorting of pancreatic endocrine progenitor cells and/or nascent pancreatic endocrine cells from a mixed cell sample containing the pancreatic endocrine progenitor cells and/or nascent pancreatic endocrine cells, wherein the SUSD2 protein or its encoding gene or an mRNA encoding a precursor of the SUSD2 protein is a marker in said identification, screening or sorting of pancreatic endocrine progenitor cells and/or nascent pancreatic endocrine cells; wherein the amino acid sequence of the SUSD2 protein has the sequence of SEQ ID NO:1 and the nucleotide sequence of the encoding gene of the SUSD2 protein is SEQ ID NO: 2; and wherein the method for screening or sorting is by detecting the expression of the SUSD2 protein, the encoding gene of SUSD2 protein, or the mRNA encoding a precursor of the SUSD2 protein through immuno magnetic bead sorting or flow cytometry sorting, and wherein the method for identification is by detecting the expression of the SUSD2 protein, the encoding gene of SUSD2 protein, or the mRNA encoding a precursor of the SUSD2 protein through immunofluorescent antibody assay or flow cytometry.

* * * * *

SEQUENCE LISTING

```
<160> NUMBER OF SEQ ID NOS: 4

<210> SEQ ID NO 1
<211> LENGTH: 822
<212> TYPE: PRT
<213> ORGANISM: Homo sapiens

<400> SEQUENCE: 1

Met Lys Pro Ala Leu Leu Pro Trp Ala Leu Leu Leu Leu Ala Thr Ala
1               5                   10                  15

Leu Gly Pro Gly Pro Gly Pro Thr Ala Asp Ala Gln Glu Ser Cys Ser
            20                  25                  30

Met Arg Cys Gly Ala Leu Asp Gly Pro Cys Ser Cys His Pro Thr Cys
        35                  40                  45

Ser Gly Leu Gly Thr Cys Cys Leu Asp Phe Arg Asp Phe Cys Leu Glu
    50                  55                  60

Ile Leu Pro Tyr Ser Gly Ser Met Met Gly Gly Lys Asp Phe Val Val
65                  70                  75                  80

Arg His Phe Lys Met Ser Ser Pro Thr Asp Ala Ser Val Ile Cys Arg
                85                  90                  95

Phe Lys Asp Ser Ile Gln Thr Leu Gly His Val Asp Ser Ser Gly Gln
            100                 105                 110

Val His Cys Val Ser Pro Leu Leu Tyr Glu Ser Gly Arg Ile Pro Phe
        115                 120                 125

Thr Val Ser Leu Asp Asn Gly His Ser Phe Pro Arg Ala Gly Thr Trp
    130                 135                 140

Leu Ala Val His Pro Asn Lys Val Ser Met Met Glu Lys Ser Glu Leu
145                 150                 155                 160

Val Asn Glu Thr Arg Trp Gln Tyr Tyr Gly Thr Ala Asn Thr Ser Gly
                165                 170                 175

Asn Leu Ser Leu Thr Trp His Val Lys Ser Leu Pro Thr Gln Thr Ile
            180                 185                 190
```

```
Thr Ile Glu Leu Trp Gly Tyr Glu Thr Gly Met Pro Tyr Ser Gln
            195                 200                 205
Glu Trp Thr Ala Lys Trp Ser Tyr Leu Tyr Pro Leu Ala Thr His Ile
    210                 215                 220
Pro Asn Ser Gly Ser Phe Thr Phe Thr Pro Lys Pro Ala Pro Pro Ser
225                 230                 235                 240
Tyr Gln Arg Trp Arg Val Gly Ala Leu Arg Ile Ile Asp Ser Lys Asn
                245                 250                 255
Tyr Ala Gly Gln Lys Asp Val Gln Ala Leu Trp Thr Asn Asp His Ala
            260                 265                 270
Leu Ala Trp His Leu Ser Asp Asp Phe Arg Glu Asp Pro Val Ala Trp
        275                 280                 285
Ala Arg Thr Gln Cys Gln Ala Trp Glu Glu Leu Glu Asp Gln Leu Pro
    290                 295                 300
Asn Phe Leu Glu Glu Leu Pro Asp Cys Pro Cys Thr Leu Thr Gln Ala
305                 310                 315                 320
Arg Ala Asp Ser Gly Arg Phe Phe Thr Asp Tyr Gly Cys Asp Met Glu
                325                 330                 335
Gln Gly Ser Val Cys Thr Tyr His Pro Gly Ala Val His Cys Val Arg
            340                 345                 350
Ser Val Gln Ala Ser Leu Arg Tyr Gly Ser Gly Gln Gln Cys Cys Tyr
        355                 360                 365
Thr Ala Asp Gly Thr Gln Leu Leu Thr Ala Asp Ser Ser Gly Gly Ser
    370                 375                 380
Thr Pro Asp Arg Gly His Asp Trp Gly Ala Pro Pro Phe Arg Thr Pro
385                 390                 395                 400
Pro Arg Val Pro Ser Met Ser His Trp Leu Tyr Asp Val Leu Ser Phe
                405                 410                 415
Tyr Tyr Cys Cys Leu Trp Ala Pro Asp Cys Pro Arg Tyr Met Gln Arg
            420                 425                 430
Arg Pro Ser Asn Asp Cys Arg Asn Tyr Arg Pro Arg Leu Ala Ser
        435                 440                 445
Ala Phe Gly Asp Pro His Phe Val Thr Phe Asp Gly Thr Asn Phe Thr
    450                 455                 460
Phe Asn Gly Arg Gly Glu Tyr Val Leu Leu Glu Ala Ala Leu Thr Asp
465                 470                 475                 480
Leu Arg Val Gln Ala Arg Ala Gln Pro Gly Thr Met Ser Asn Gly Thr
                485                 490                 495
Glu Thr Arg Gly Thr Gly Leu Thr Ala Val Ala Val Gln Glu Gly Asn
            500                 505                 510
Ser Asp Val Val Glu Val Arg Leu Ala Asn Arg Thr Gly Gly Leu Glu
        515                 520                 525
Val Leu Leu Asn Gln Glu Val Leu Ser Phe Thr Glu Gln Ser Trp Met
    530                 535                 540
Asp Leu Lys Gly Met Phe Leu Ser Val Ala Ala Gly Asp Arg Val Ser
545                 550                 555                 560
Ile Met Leu Ala Ser Gly Ala Gly Leu Glu Val Ser Val Gln Gly Pro
                565                 570                 575
Phe Leu Ser Val Ser Val Leu Leu Pro Glu Lys Phe Leu Thr His Thr
            580                 585                 590
His Gly Leu Leu Gly Thr Leu Asn Asn Asp Pro Thr Asp Asp Phe Thr
        595                 600                 605
Leu His Ser Gly Arg Val Leu Pro Pro Gly Thr Ser Pro Gln Glu Leu
```

```
            610              615                 620

Phe Leu Phe Gly Ala Asn Trp Thr Val His Asn Ala Ser Ser Leu Leu
     625                 630                 635                 640

Thr Tyr Asp Ser Trp Phe Leu Val His Asn Phe Leu Tyr Gln Pro Lys
                     645                 650                 655

His Asp Pro Thr Phe Glu Pro Leu Phe Pro Ser Glu Thr Thr Leu Asn
                 660                 665                 670

Pro Ser Leu Ala Gln Glu Ala Ala Lys Leu Cys Gly Asp Asp His Phe
                 675                 680                 685

Cys Asn Phe Asp Val Ala Ala Thr Gly Ser Leu Ser Thr Gly Thr Ala
                 690                 695                 700

Thr Arg Val Ala His Gln Leu His Gln Arg Arg Met Gln Ser Leu Gln
     705                 710                 715                 720

Pro Val Val Ser Cys Gly Trp Leu Ala Pro Pro Asn Gly Gln Lys
                     725                 730                 735

Glu Gly Asn Arg Tyr Leu Ala Gly Ser Thr Ile Tyr Phe His Cys Asp
                 740                 745                 750

Asn Gly Tyr Ser Leu Ala Gly Ala Glu Thr Ser Thr Cys Gln Ala Asp
                 755                 760                 765

Gly Thr Trp Ser Ser Pro Thr Pro Lys Cys Gln Pro Gly Arg Ser Tyr
                 770                 775                 780

Ala Val Leu Leu Gly Ile Ile Phe Gly Gly Leu Ala Val Val Ala Ala
     785                 790                 795                 800

Val Ala Leu Val Tyr Val Leu Arg Arg Arg Lys Gly Asn Thr His
                     805                 810                 815

Val Trp Gly Ala Gln Pro
                 820

<210> SEQ ID NO 2
<211> LENGTH: 3201
<212> TYPE: DNA
<213> ORGANISM: Homo sapiens

<400> SEQUENCE: 2
gcctcggagc cactgcactg ctggctgcag acacaggctg caccatgaag ccagccctcc      60
tgccctgggc cctgctgctg ctggcgacag ccctcggccc gggccccgga cccacagcag     120
atgcccaaga gagctgctcc atgcgctgtg gcgccctgga cggccatgt tcctgccacc      180 cgacgtgctc tggccttggc acctgctgct ggatttccg ggacttctgc ctggagatat      240
tgccctactc aggatccatg atgggcggca aggactttgt ggtgcggcac ttcaagatgt      300
ccagccccac agacgccagt gtgatctgca ggtttaagga cagcatccag accctcggcc      360
atgtggactc ctccgggcaa gtgcactgtg tgtcacctct gctctatgag agcggccgca      420
tccccttcac tgtgtcactg gacaacggcc actccttccc tcgtgcgggc acctggctgg      480
ctgtgcaccc caacaaagtg tcaatgatgg agaagagcga gttggtgaac gagacgcgtt      540
ggcaatacta cggcaccgcc aacacctcag gcaacctcag cctgacctgg catgtcaagt      600
cgctgcccac gcagaccatc accatcgaac tgtggggcta cgaggagaca ggaatgccct      660
actcacagga gtggactgca aagtggtcgt acctgtaccc cctggccaca cacatcccca      720
actccggctc tttcactttc accccaaaac tgctcctcc cagctaccag agatggcgag      780
tgggtgcact tcgatcatc gacagcaaaa attacgcagg gcagaaggac gtgcaggcgc      840
tctggaccaa cgaccacgca ctggcctggc acctgagcga tgacttccga gaggaccctg      900
```

```
tggcctgggc acgaactcag tgccaggcct gggaggagct ggaggatcag ctgcccaact      960
tcctggagga gctgccggac tgcccctgca ccctgaccca ggcccgggct gactccggcc     1020
gcttcttcac ggactacggc tgtgacatgg agcagggcag cgtgtgcacc taccaccccg     1080
gggccgtgca ctgtgtgcgt tctgtgcagg ccagcctccg gtacggctca ggtcagcagt     1140
gctgctacac agcggacggg acgcagctcc tgacagctga ctccagcggc ggcagcactc     1200
ccgaccgcgg ccatgactgg ggcgcacccc cgttccgcac gccacccega gtgcccagca     1260
tgtcccactg gctctacgat gtcctcagct tctattactg ctgcctctgg gcacccgact     1320
gccccgcta catgcaacgg cggccctcca atgactgccg caactaccgg cccccaagac     1380
tggcctccgc cttcggagac ccacactttg tgaccttcga cggcaccaac ttcacattca     1440
atgggcgcgg agagtacgtg ctgctggagg cagcgctgac cgacctgagg gtgcaggcgc     1500
gggcccagcc cgggacgatg tccaacggca cggagacccg tggcactggg ctgaccgcag     1560
tggccgtcca ggagggcaac tcagatgtgg tggaagtcag gctggccaac aggaccggag     1620
gtctggaggt gctgctgaac caggaggtgc tgagcttcac cgagcagagc tggatggacc     1680
tgaaaggaat gttcctgtcg gtggctgccg gggacagggt ctccatcatg ctggcatcag     1740
gggccggcct ggaggtcagc gtgcagggcc gttcctgag tgtgtccgtc ctgctgcctg     1800
agaagttcct cacccacacc cacggcctcc tcgggacact caacaacgac cccaccgacg     1860
acttcaccct gcacagcggg cgcgtcctgc ccccaggcac cagtcccag gagctgttcc      1920
tgtttgggc caactggacc gtgcacaatg cgtcctccct gctcacctac gattcctggt     1980
tcctggtcca caacttcctg taccaaccca agcacgaccc caccttcgag cccctcttcc     2040
ccagtgagac caccctcaac cccagcctgg cacaagaggc agccaaacta tgtggggacg     2100
atcatttctg caactttgat gtggcagcca ctgggagcct gagcacgggc actgccactc     2160
gggtggccca ccagctgcac cagcgtcgca tgcagagcct gcagccagtg gtgtcctgtg     2220
gctggctggc cccacctccc aacggacaaa aggagggcaa caggtacctg gcgggttcca     2280
ccatctactt ccactgtgac aacggctaca gcctggccgg ggcagagacc agcacctgcc     2340
aggctgacgg cacctggtcc tcacccacc cgaagtgcca gccaggacgc agctacgcgg     2400
tgctgttggg catcatcttt gggggcctcg cggtggtggc ggcggttgcg ctcgtctatg     2460
tgctgctgcg ccgcaggaag ggcaacacgc acgtctgggg tgcacagccc tgatgggagc     2520
agcttggctg tgagcaccag gccaagactc ctgagaacag gcagcccagt cctgcgactc     2580
ccgcatcccc aggaccagac acctgggacc tggatacttg atacctgggc atttaacccc     2640
ctactctgtc atctcagacc ccaggcagga ggcccagtgt tccaacaccc aagcccgtg     2700
ctagcagcgc tccgtgctct tccccaaata ctcacggctc taattcccca aacctgaaac     2760
ttcatacect gggattctaa tacctatgtc ctgagccctg acactccac acctgagcct     2820
cagattccaa tagctcactc cctagagcct gacgccgggg cccctgaccc ctgagcctca     2880
gattccaata cctcactccc cagagcctga tgccggggcc cctgacccct gatctacgga     2940
ggcctgctcc cggaccgtgc gggcaccagt gcagtgctgc cttggttcct ggaccctgg      3000
gcccatcctg gaccccagaa tggggtaagg agaggcccca gaaccccaaa gcagacagcg     3060
agacccccag cggcagaggc ctccctcggc actccaggct tataatttcg aactcttctg     3120
gaaggtcact caggaacacc ctccctgcct gtgcaaagag aaaacaagcg ccttgtttcc     3180
ttcaaaaaaa aaaaaaaaaa a                                                3201
```

```
<210> SEQ ID NO 3
<211> LENGTH: 18
<212> TYPE: DNA
<213> ORGANISM: Artificial Sequence
<220> FEATURE:
<223> OTHER INFORMATION: Synthetic Primer

<400> SEQUENCE: 3
ggcaccgcca acacctca                                                  18

<210> SEQ ID NO 4
<211> LENGTH: 18
<212> TYPE: DNA
<213> ORGANISM: Artificial Sequence
<220> FEATURE:
<223> OTHER INFORMATION: Synthetic Primer

<400> SEQUENCE: 4
gcgtgggcag cgacttga                                                  18
```